US011399775B2

(12) United States Patent
Stephens

(10) Patent No.: US 11,399,775 B2
(45) Date of Patent: Aug. 2, 2022

(54) SYSTEMS AND METHODS TO DETECT CARDIAC EVENTS

(71) Applicant: Verily Life Sciences LLC, South San Francisco, CA (US)

(72) Inventor: Philip Stephens, Niwot, CO (US)

(73) Assignee: Verily Life Sciences LLC, South San Francisco, CA (US)

(*) Notice: Subject to any disclaimer, the term of this patent is extended or adjusted under 35 U.S.C. 154(b) by 163 days.

(21) Appl. No.: 16/544,719

(22) Filed: Aug. 19, 2019

(65) Prior Publication Data
US 2021/0052229 A1   Feb. 25, 2021

(51) Int. Cl.
*A61B 5/00* (2006.01)
*A61B 5/024* (2006.01)
(Continued)

(52) U.S. Cl.
CPC ........ *A61B 5/7275* (2013.01); *A61B 5/02416* (2013.01); *A61B 5/02438* (2013.01);
(Continued)

(58) Field of Classification Search
CPC . A61B 5/02416; A61B 5/02438; A61B 5/349; A61B 5/318; A61B 5/361;
(Continued)

(56) References Cited

U.S. PATENT DOCUMENTS 10,398,381 B1 * 9/2019 Heneghan ............ A61B 5/0261
2015/0164355 A1 * 6/2015 Brockway .............. A61B 5/363
600/479
(Continued)

FOREIGN PATENT DOCUMENTS

EP   3318184 A1   5/2018

OTHER PUBLICATIONS

Partial International Search Report dated Oct. 14, 2020 for corresponding International Patent Application No. PCT/US2020/044138, 13 pages.
(Continued)

*Primary Examiner* — Carl H Layno
*Assistant Examiner* — Jane C Kalinock
(74) *Attorney, Agent, or Firm* — Christensen O'Connor Johnson Kindness PLLC

(57) ABSTRACT

In some embodiments, features related to inter-beat intervals (IBI) detected by a PPG sensor of a wearable device are extracted and provided to a cardiovascular classifier in order to detect likely instances of a cardiac condition such as atrial fibrillation. Some embodiments use features related to the entropy of the IBI data to improve the predictions generated by the cardiovascular classifier. In some embodiments, co-information between the IBI data and IBI data gathered from healthy and AF populations is determined in order to derive features that represent the probability that a given sample of IBI data represents AF or a normal sinus rhythm. In response to determining likely instances of AF based on these features, the wearable device may obtain clinically acceptable data, such as an ECG, to be transmitted to a separate device for review by a clinician.

20 Claims, 9 Drawing Sheets

(51) Int. Cl.
 A61B 5/046 (2006.01)
 A61B 5/361 (2021.01)
(52) U.S. Cl.
 CPC .............. *A61B 5/361* (2021.01); *A61B 5/681* (2013.01); *A61B 5/7267* (2013.01)
(58) Field of Classification Search
 CPC ..... A61B 5/681; A61B 5/7264; A61B 5/7267; A61B 5/7275; A61B 5/7282; A61B 2560/029; G16H 40/63; G16H 50/20
 USPC ........................................................ 600/301
 See application file for complete search history.

(56) References Cited

U.S. PATENT DOCUMENTS

| | | | |
|---|---|---|---|
| 2017/0014037 | A1 | 1/2017 | Coppola et al. |
| 2018/0000428 | A1* | 1/2018 | Swiston ............. A61B 5/02055 |
| 2018/0279891 | A1 | 4/2018 | Miao et al. |
| 2019/0159676 | A1 | 5/2019 | Murphy et al. |
| 2020/0113459 | A1 | 4/2020 | Jäntti et al. |
| 2020/0138306 | A1* | 5/2020 | Li ........................... G16H 50/20 |

OTHER PUBLICATIONS

International Search Report and Written Opinion dated Dec. 9, 2020, in corresponding International Patent Application No. PCT/US2020/044138, 18 pages.

\* cited by examiner

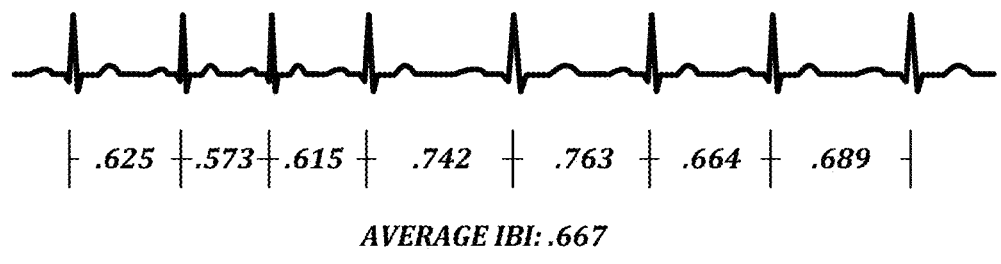
AVERAGE IBI: .667
FIG. 7A
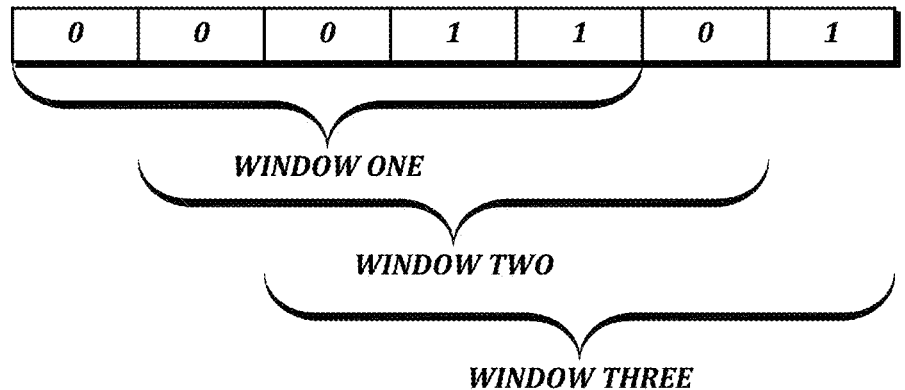
FIG. 7B
| # | VALUE (BINARY) | VALUE (BASE 10) |
|---|---|---|
| 1 | 00011 | 3 |
| 2 | 00110 | 6 |
| 3 | 01101 | 13 |
FIG. 7C

SYSTEMS AND METHODS TO DETECT CARDIAC EVENTS

TECHNICAL FIELD

This disclosure relates generally to cardiac monitoring, and in particular but not exclusively relates to techniques for improving cardiac monitoring by wearable devices.

BACKGROUND

A variety of cardiovascular parameters or other information about the health state of a person can be detected by a wearable device that is mounted to the person's body. Such a wearable device can operate one or more sensors to continuously detect information about the person's body. Such continuous monitoring can provide an increased amount of data to improve the determination of information about the person's health state, e.g., by increasing a confidence level of a health state determination. Additionally, by continuously monitoring the person across extended periods of time and/or across a variety of activities of the person, rare physiological events can be detected. Such rare events could be indicative of a serious health condition, e.g., atrial fibrillation.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a wearable device is provided. The wearable device comprises a first sensor, a second sensor, and a controller. The controller has logic configured to, in response to execution by the controller, cause the wearable device to perform actions comprising analyzing a signal generated by the first sensor to determine a heartbeat characteristic for a subject; comparing entropy in the heartbeat characteristic to entropy in heartbeat characteristic information for a population associated with a cardiac condition to determine a probability that the heartbeat characteristic is similar to the heartbeat characteristic information for the population; providing the probability as a feature to a cardiovascular classifier to determine whether the heartbeat characteristic is associated with the cardiac condition; and in response to determining that the heartbeat characteristic is associated with the cardiac condition, collecting information using the second sensor.

In some embodiments, a non-transitory computer-readable medium is provided. The computer-readable medium has computer-executable instructions stored thereon that, in response to execution by one or more processors of a computing device, cause the computing device to perform actions for detecting a cardiac condition. The computing device computes an average inter-beat interval (IBI) value for a series of IBI values from a first time segment. The computing device creates a series of binary values that indicate whether or not the IBI values of the series of IBI values are greater than the average IBI value. The computing device generates a sequence of window values based on a sliding window over the series of binary values. The computing device determines a probability of whether the sequence of window values belongs to a data set associated with the cardiac condition. The computing device provides the probability to a cardiovascular classifier to determine a label that indicates whether the first time segment is associated with the cardiac condition.

In some embodiments, a non-transitory computer-readable medium is provided. The computer-readable medium has computer-executable instructions stored thereon that, in response to execution by one or more processors of a computing system, cause the computing system to perform actions for training a cardiovascular classifier to detect a cardiac condition. The computing system receives a series of inter-beat interval (IBI) values collected from subjects of at least one population associated with the cardiac condition. The computing system generates representations of entropy within the series of IBI values. The computing system stores the representations of entropy in a data store associated with the at least one population. For each subject, the computing system compares a representation of entropy in at least a portion of the series of IBI values for the subject with the representations of entropy in the data store associated with the at least one population to determine a probability that the portion of the series of IBI values is associated with the representations of entropy in the data store; and stores the probability as a feature associated with the subject in a set of training data. The computing system trains a cardiovascular classifier using the set of training data.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7A-7C illustrate a non-limiting example embodiment of the results of the procedure of FIG. 6 being executed over a given series of IBI values;

DETAILED DESCRIPTION

Overview

Figure 1A:
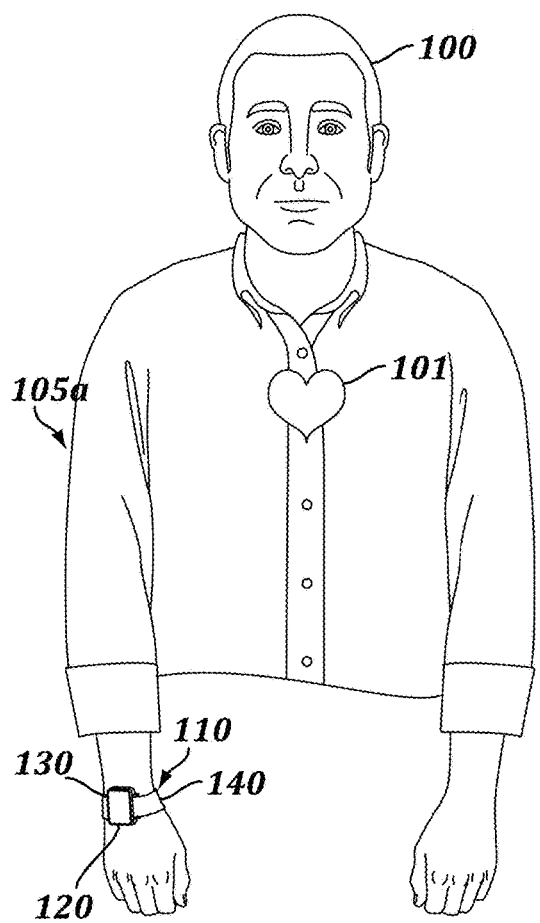
FIG. 1A illustrates a non-limiting example embodiment of a wearable device according to various aspects of the present disclosure, mounted to a wrist of a first arm of a wearer during a first period of time.

It can be beneficial to continuously monitor a subject for the occurrence of certain health events, e.g., cardiovascular events. For example, it could be beneficial to monitor for ventricular or atrial fibrillation, tachycardia, bradycardia, or other arrhythmic events.

Detection of cardiac conditions via continuous monitoring can facilitate prompt emergency medical attention, administration of a drug or other therapy, or improved detection of information about the cardiovascular condition. For example, in response to determining that a continuously monitored signal is indicative that a cardiovascular event is occurring, a person could be prompted to perform a diagnostic activity, to apply pressure to a device or sensor (e.g., to improve a noise level or other property of signals generated by the sensor), to touch an electrode of a device to facilitate detection of electrocardiographic signals, or to perform some other task or activity. Such additional signals or information about the cardiovascular event could be used to diagnose a health condition, to determine a dose of a drug or other treatment, to determine information about the efficacy of a drug, to determine information about a disease (e.g., a population distribution of properties of the disease), or to determine some other useful information.

In order to detect cardiac conditions such as atrial fibrillation (AF), one or more sensors could be incorporated into a wearable device and worn by a subject. The one or more sensors could be operated to detect pulse rates, time-varying blood volume in subsurface vasculature, electrocardiographic signals, the acceleration or rotation of a body part, ambient light levels, or other signals that could be used to determine whether a cardiovascular event is occurring. The determination of whether a cardiovascular event is occurring could involve use of a cardiovascular classifier to determine whether one or more sensor signals are indicative of the cardiovascular event. For example, one or more sensor signals could be used to determine an activity of the wearer, and the determined activity could be used in combination with some other sensor signal to determine whether a cardiovascular event is occurring. When the device, using the cardiovascular classifier, determines that a cardiovascular event is occurring, the device could operate to prompt the wearer to perform some action, e.g., to touch an electrode of the device to facilitate detection of an electrocardiographic waveform, to perform a diagnostic activity.

One main issue with regard to monitoring for cardiovascular events or conditions using a wearable device relates to managing a balance between battery life and accuracy. Some existing wearable devices may pair a single-lead ECG with a wearable device that includes a photoplethysmograph (PPG) sensor. However, battery life on such devices is exceedingly low, particularly while monitoring for cardiovascular conditions. This causes such devices to only perform checks for cardiovascular conditions at long intervals in order to conserve battery, and the time needed to recharge causes gaps to appear in the monitoring data. Other devices include only a PPG sensor and have better battery life. However, only having the PPG sensor as the sole modality for detecting cardiovascular conditions cannot provide clinically acceptable results. Implantable loop recorders may be able to provide continuous ECG readings for up to three years, but are expensive and invasive. Likewise, mobile cardiac telemetry (ECG) patches are also expensive, and are not generally suited to long-term monitoring.

Having access to long-term collections of high-quality data is important in accurately detecting cardiac conditions. Using a low-power, lower-quality sensor (such as a PPG sensor) to continuously monitor for a cardiac condition, and then prompting the subject to collect a more detailed signal with a higher-power, higher-quality sensor (such as an ECG sensor) if the PPG sensor data indicates that the condition is likely present can help provide the balance between data accuracy and battery life. However, the incidence of false positives (i.e., situations wherein a signal appears to be indicative of a cardiovascular event, but no cardiovascular event is occurring) can result in unnecessary prompting of a user to obtain detailed information, reducing wearer compliance with the prompts, or causing other unwanted effects. Further, the incidence of false negatives (i.e., situation wherein a cardiovascular event is occurring but a system does not detect the event) can result in reduced collection of event-related data, delayed medical treatment, or other unwanted effects. What is desired are techniques for improving the predictions provided with respect to the PPG sensor information in order to improve battery life and therefore improve the availability of high-quality data for diagnosing cardiac conditions.

Training and Using Classifiers to Detect Cardiac Conditions

In order to reduce the incidence of false positives and/or false negatives, a cardiovascular classifier can be generated based on extensive data from one or more devices (e.g., from devices collecting data from one or more wearers), data from clinical data acquisition systems, or other data sources. Further, the cardiovascular classifier used by a wearable device could be updated over time, e.g., based on signals detected by the wearable device. Further, the cardiovascular classifier may be provided to the wearable device, such that the wearable device can independently classify cardiac activity.

Accessing such extensive sources of data (e.g., from clinical systems, from many other wearable devices) and using such data to generate a cardiovascular classifier could require an amount of data storage, an amount of processor power, access to remote databases, or other factors that are difficult or impractical to provide in the wearable device itself. Instead, a wearable device could upload sensor data to a cloud computing service, a computer at a physician's office or hospital, or some other remote server. The remote server could then use the sensor data from the wearable device, along with additional data (e.g., data from other wearable devices, data from clinical data acquisition systems, data from previous clinical studies or other sources of population data), to generate a cardiovascular classifier. The remote server could then transmit the determined cardiovascular classifier to the wearable device, and the wearable device could use the cardiovascular classifier to determine whether sensor signals generated by the wearable device are indicative of a cardiovascular event. The wearable device could also receive updated cardiovascular classifiers from the remote server, e.g., cardiovascular classifiers that have been updated based on additional sensor data received from the wearable device, from other wearable devices, or from some other source.

A wearable device, e.g., a wrist-mountable device, could include one or more sensors configured to detect physical variables (e.g., to illuminate a portion of subsurface vasculature and detect a volume of blood in the portion of subsurface vasculature based on a detected intensity of responsively emitted light) that are related to the occurrence or non-occurrence of a cardiovascular event of interest. Such cardiovascular events could include atrial or ventricular fibrillation, tachycardia, bradycardia, or other arrhythmias, acute hypertension or hypotension, incidents of postural orthostatic tachycardia syndrome, incidents of clinical or subclinical cardiac arrest or ischemia, extra heart beats, or other events of interest. It could be beneficial to use such a wearable device to continuously monitor a wearer in order to detect the occurrence of such events. Such detection could permit more prompt delivery of medical care, timed application of a drug or other medical treatment, detection of additional information about rare events, or some other beneficial applications.

A variety of physiological or other signals related to a cardiovascular event or to some physiological event or process of interest could be detected and used to determine whether such an event is occurring as described herein. In some examples, such signals could be directly related to the event or process of interest, e.g., a photoplethysmographic signal, electrocardiographic signal, or other signal related to pulse timing, pulse rate, electrical activity of the heart, or some other process that is related to tachycardia or some other arrhythmic condition. Additionally or alternatively, the signals could be related to factors surrounding the process or event of interest, or could provide a context that could facilitate detection of an event of interest. For example, an ambient light level, an orientation, acceleration, or rotation of a body segment over time, a galvanic skin resistance, a temperature, or some other signals could be used to determine an activity of a wearer, e.g., to determine whether the wearer is resting, walking, sleeping, eating, exercising, or engaging in some other activity. Such a determined activity could then be used to determine whether a sensor signal is indicative of a cardiovascular event.

For example, a particular detected pulse rate, pulse rate variability, or other signal of interest could be within a range of expected values if a wearer is determined to be exercising. However, if the particular detected pulse rate, pulse rate variability, or other signal of interest is detected while the wearer is sleeping, resting, or otherwise engaged in a non-strenuous activity, it could be indicative that the wearer is experiencing tachycardia, myocardial infarction, or some other cardiovascular event. In such an example, the wearer could be prompted to seek medical attention, to take a drug, to facilitate detection of electrocardiographic or other signals of interest related to the event, or to take some other action.

When a device has determined (using a cardiovascular classifier or other algorithm) that the output of one or more sensors is indicative of a cardiovascular event, the device may responsively perform some additional operations. For example, the device could prompt a user to seek medical attention, prompt the user to perform a diagnostic task (e.g., to interact with a user interface of the device, to perform a sit-and-stand task), prompt the user to interact with the device in some way (e.g., to facilitate detection of an electrocardiographic waveform or other signal of interest), operate an additional sensor of the device (e.g., a sensor whose operation has a high power budget) or operate a sensor in a higher-power mode, or perform some other operations.

The device could prompt a user to interact with a sensor of the device in order to permit the detection of a signal of interest and/or to improve a noise level, accuracy, or other quality of a detected signal of interest. For example, the user could be prompted to apply pressure to the device to improve a level of coupling between a sensor and skin of the wearer, to align a sensor with a part of the wearer's body, to control a degree of perfusion of subsurface vasculature, to control a pressure applied to subsurface vasculature (e.g., to detect a blood pressure), or to perform some other action.

As an example, a wearable device could be configured to mount to a first wrist (e.g., the left wrist) of the wearer and to have a first electrical contact configured to contact a first skin location on the first wrist. The wearable device could further include a second electrical contact configured to be contacted by a second skin location of the wearer. That is, the wearer could move a portion of the wearer's body (e.g., a right hand) proximate to the wearable device such that a second skin location (e.g., a finger, hand, or wrist location of the arm of the wearer opposite the arm to which the wearable device is mounted) is in contact with the second electrical contact of the wearable device. In this way, the wearable device could enable periodic extraction of electrocardiographic signals from voltage fluctuations between the two skin locations (e.g., between a wrist location of the left arm and a finger location of the right arm). Such a wearable device could be configured in the form of a wristwatch or other wrist-mounted device (i.e., having a central housing (on or within which could be mounted first and/or second electrical contacts) mounted to the wrist by e.g., a strap or band configured to encircle the wrist) and could include means for performing additional functions, e.g., indicating a time and/or pulse rates to the wearer, prompting the wearer to contact the electrode(s), etc.

FIG. 1A illustrates a non-limiting example embodiment of a wearable device 110 according to various aspects of the present disclosure, mounted to a wrist of a first arm 105a of a wearer 100 during a first period of time. The wearable device 110 includes a housing 120 mounted to the wrist of the first arm 105a by a mount 140 (e.g., a strap or band). The wearable device further includes first (not shown) and second 130 electrical contacts. The first electrical contact is disposed on an inside (i.e., wrist-facing) side of the housing 120 and configured to contact skin at a first external body surface (i.e., skin of the wrist of the first arm 105a) when the housing 120 is mounted on the wrist of the first arm 105a. The second electrical contact 130 is configured to be contacted by skin of a second external body surface (e.g., by finger, hand, wrist, or other skin of a second arm 105b of the wearer 100). The wearable device 110 additionally includes electronics (e.g., a signal conditioner or other elements of a sensor, not shown) electrically connected to the first and second 130 electrical contacts and configured to extract an electrocardiographic waveform (related to a cardiovascular pulse of the heart 101 of the wearer 100) from voltage fluctuations between the first and second 130 electrical contacts.

Figure 1B:
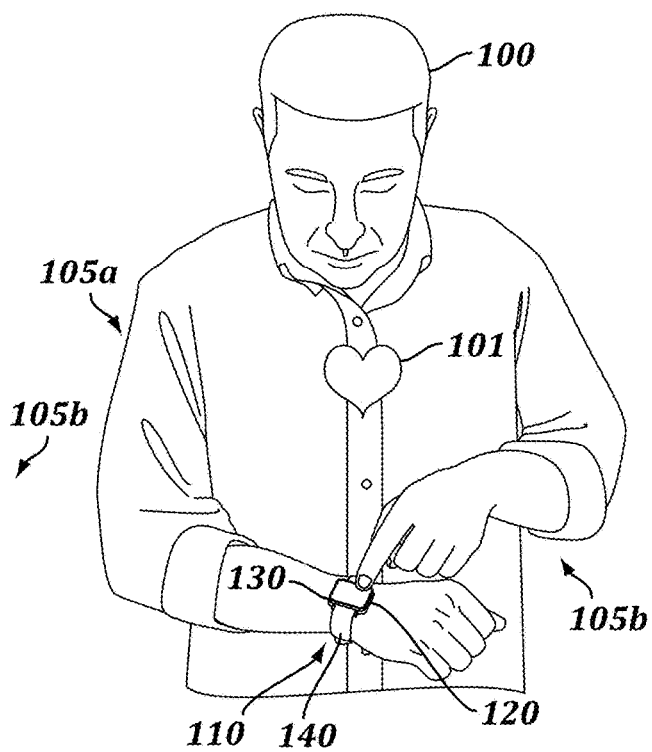
FIG. 1B illustrates the wearable device and wearer during a second period of time when the wearer is positioning skin of a finger of the second arm in contact with the second electrical contact.

FIG. 1B illustrates the wearable device 110 and wearer 100 during a second period of time when the wearer 100 is positioning skin of a finger of the second arm 105b in contact with the second electrical contact 130. In this state, electronics (e.g., a signal conditioner) of the wearable device 110 could extract an electrocardiographic waveform related to the cardiovascular pulse of the wearer's 100 heart 101 during the second period of time from voltage fluctuations between the first and second 130 electrical contacts.

Figure 1C:
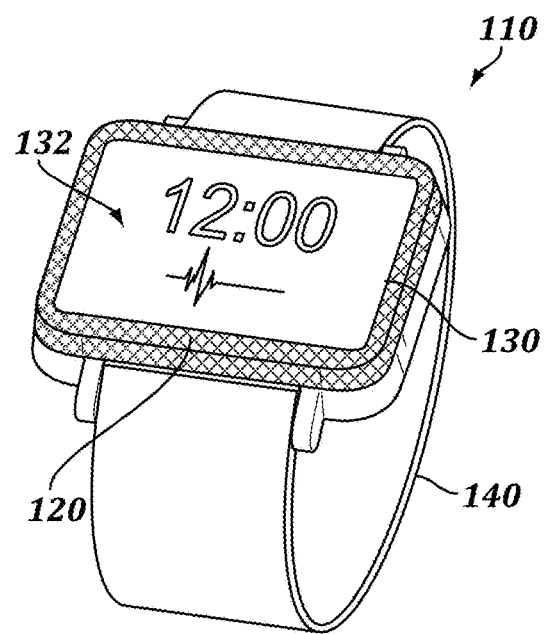
FIG. 1C illustrates the wearable device in detail.

FIG. 1C illustrates the wearable device 110 in detail. The housing 120 has an outside surface that is away from the first external surface of the body and an inside surface (not shown) that is toward and/or in contact with the first external surface of the body when the housing 120 is positioned on the first external surface of the body. A user interface 132 is disposed on the outside surface of the housing 120. The second electrical contact 130 is disposed along an edge of the outside surface of the housing 110*d* completely enclosing the user interface 132. Other configurations of a wearable device as described herein are anticipated.

Signals from the first and second electrical contact 130 could be detected and assessed to determine whether a signal of interest can be reliably determined from a sensor. This could include determining a power level of the detected signal, a signal to noise ratio of the detected signal (e.g., a power in frequency bands corresponding to a cardiovascular pulse or other signal of interest divided by total signal power), a power of the signal within one or more frequency bands (e.g., within frequency bands related to noise content of the signal), a variability of a pulse rate or pulse period determined based on the signal, a quality and/or presence of a feature in the signal (e.g., a QRS complex in the signal), or some other determination related to whether a signal of interest can be reliably determined from the sensor output. Additionally or alternatively, some additional variable related to the signal of interest could be detected and used to determine whether a signal of interest can be reliably determined from the sensor output. For example, an impedance between electrodes of an electrocardiogram sensor, a pressure or force between a sensor and a skin surface, or some other variables related to the use of a sensor to detect the signal of interest could be detected and used to determine whether the signal of interest can be reliably detected using the sensor.

A cardiovascular classifier can be used to determine whether one or more sensor signals are indicative of the cardiovascular event of interest. A cardiovascular classifier can apply thresholds, filters, pattern-matching templates, linear or nonlinear kernels or transforms, finite state machines, statistical inference, or other algorithms or techniques, individually or in combination, to determine whether a cardiovascular event is occurring, or is likely occurring, based on one or more sensor signals detected from a wearer's body and/or from an environment of the wearer. Such a determination could include generating a binary output related to the presence of the cardiovascular event and/or generating a likelihood or other value corresponding to the probability, in view of one or more sensor signals, that the cardiovascular event is occurring.

Using a cardiovascular classifier to determine whether a signal is indicative of a cardiovascular event could include transforming the signal in some way and/or determining some representative information about the signal. For example, the signal could be bandpass filtered, lowpass filtered, highpass filtered, applied to a moving-average filter, convolved with a matching filter, thresholded, applied to a polynomial, or filtered or modified in some other way. The signal could be resampled or separated into discrete overlapping or non-overlapping portions (e.g., into individual portions corresponding to respective different heart beats). The signal could be transformed, e.g., using the Fourier transform, the Laplace transform, a wavelet transform, or some other transformation to generate frequency components or other transformed information about the signal. Pulses, peaks, heart beats, electrocardiographic complexes, or other features could be detected within the signal and used to generate information about the signals, e.g., to determine the presence or timing of the features, to determine a shape of the features, to determine a rate of occurrence of a feature and/or to determine a variability of such a rate over time, to determine a deviation of the shape of the features from a template, or to determine some other information about features in the signal.

Using a cardiovascular classifier to determine whether a signal is indicative of a cardiovascular event could include using a linear or nonlinear kernel or matrix to generate an output based on a vector of inputs related to the sensor signal (e.g., based on a vector of samples of the signal, based on a vector of frequency components of the signal, based on a vector of properties of pulses or other features within the signal). For example, linear or nonlinear principal components analysis, independent component analysis, a support vector machine, or some other algorithm could be used to determine one or more output values based on a signal. Such output values could then be thresholded, applied to a sigmoid or other nonlinear function, or used in some other manner according to the cardiovascular classifier to determine whether the sensor signal is indicative of the cardiovascular event of interest.

Using a cardiovascular classifier to determine whether a signal is indicative of a cardiovascular event could include using pattern matching to determine whether the signal, or some information determined from the signal, is indicative of the cardiovascular event. This could include determining a degree similarity between the sensor signal, frequency components of the sensor signal, an output of another element of the classifier (e.g., the output of a principal components analysis), or some other information related to the signal and a template pattern. Such a degree of similarity could be used to determine that the cardiovascular event is occurring and/or to determine the likelihood that the cardiovascular event is occurring. Additionally or alternatively, a template pattern could be convolved with the signal and/or with an output determined from the signal and the result of the convolution could be used to determine whether the signal is indicative of the cardiovascular event (e.g., if the output of the convolution exceeds a threshold value for more than a threshold duration). Additionally or alternatively, such pattern matching could be used to detect features within the sensor signal and/or to determine information about such features (e.g., to determine a character of the deviation of such features from a template pattern).

Using a cardiovascular classifier to determine whether a signal is indicative of a cardiovascular event could include using multiple signals to detect the occurrence or likelihood of occurrence of the cardiovascular event. This could include applying two or more signals to respective elements of the cardiovascular classifier (e.g., to respective principal components analyses) and combining the outputs of the elements (e.g., by element-wise multiplication of outputs of respective different principal components analyses) or combining the information from two different signals in some other way (e.g., by convolving the signals together). Additionally or alternatively, one or more of the signals could be used to set a filter parameter, finite state machine state, operating mode, internal variable, or other property of operation of the cardiovascular classifier which could then be used to determine whether some additional or alternative one or more of the signals is indicative of the cardiovascular event. For example, one or more signals (e.g., accelerometer signals, gyroscope signals, ambient light signals) could be used to determine an activity of the wearer (e.g., sleeping, exercising, walking, sitting, eating). The cardiovascular classifier could then determine, based on the detected activity, whether some other sensor signal is indicative of the cardiovascular event In some embodiments, the cardiovascular classifier may include a machine learning model that accepts features based on the signals as input and outputs labels for the signals. The machine learning model may include any suitable type of machine learning model for generating such labels, including but not limited to a support vector machine, a neural network, a decision tree, a naïve Bayes classifier, and a nearest neighbor method. Such a machine learning model may be trained using any suitable supervised learning technique, including but not limited to gradient descent. In some embodiments, specific features may be extracted from the signals and provided to the cardiovascular classifier in order to improve detection of specific cardiac conditions. Some example features for improving detection of atrial fibrillation are described in further detail below.

It can be beneficial to reduce the false-positive detection of such cardiovascular events (e.g., to improve wearer compliance with performing diagnostic tasks or providing improved sensor signals) and to reduce the false-negative non-detection of such events (e.g., to prevent loss of data about an event of interest). To improve the detection of cardiovascular events, based on continuous monitoring of one or more related physiological properties or processes related thereto, the cardiovascular classifier could be determined and/or updated based on sensor data from one or more wearable devices or from other sources of information (e.g., clinical data acquisition systems). The cardiovascular classifier for a particular device of a particular wearer could be determined based on days, months, or years of sensor data detected by one or more wearable device(s) of the particular wearer. The cardiovascular classifier for a particular device of a particular wearer could also be determined based on data from other persons (e.g., data from wearable devices of other wearers). For example, the cardiovascular classifier could be determined based on information from clinical data acquisition systems (e.g., Holter monitors) that are applied and operated by clinicians and/or from a population of wearers using respective wearable devices as described herein.

The cardiovascular classifier could be updated over time, based on additional sensor signals received from one or more wearable devices or from some other systems (e.g., clinical data acquisition systems). Such updates could occur semi-continuously or according to some other timing. The cardiovascular classifier could be updated based on signals used to confirm that a particular sensor signal was indicative of a cardiovascular event. For example, a first instance of a cardiovascular signal could be used to determine that a first sensor signal is indicative of a cardiovascular event. In response to that determination, a wearable device could provide a prompt to a wearer such that an electrocardiographic waveform or other signal related to the putative based cardiovascular event is detected. The detected electrocardiographic waveform or other related signal could then be used to determine whether the first sensor signal was actually indicative of the cardiovascular event and that determination could be used to update the cardiovascular classifier.

Using such extensive and/or various data to generate and/or update a cardiovascular classifier could require an amount of data storage, an amount of processor power, access to remote databases, or other factors such that it is not feasible for the cardiovascular classifier to be generated and/or updated by a wearable device. Rather, such a wearable device could upload sensor data to a cloud computing service, a computer at a physician's office or hospital, or some other remote server. The remote server could then use the sensor data from the wearable device, along with additional data (e.g., data from other wearable devices, data from clinical data acquisition systems, data from previous clinical studies or other sources of population data, features derived from the sensor data), to generate a cardiovascular classifier. The remote server could then transmit the determined cardiovascular classifier to the wearable device, and the wearable device could use the cardiovascular classifier to determine whether future sensor signals generated by the wearable device are indicative of a cardiovascular event. The wearable device could also receive updated cardiovascular classifiers from the remote server, e.g., cardiovascular classifiers that have been updated based on additional sensor data received from the wearable device, from other wearable devices, or from some other source.

Example Devices

Figure 2:
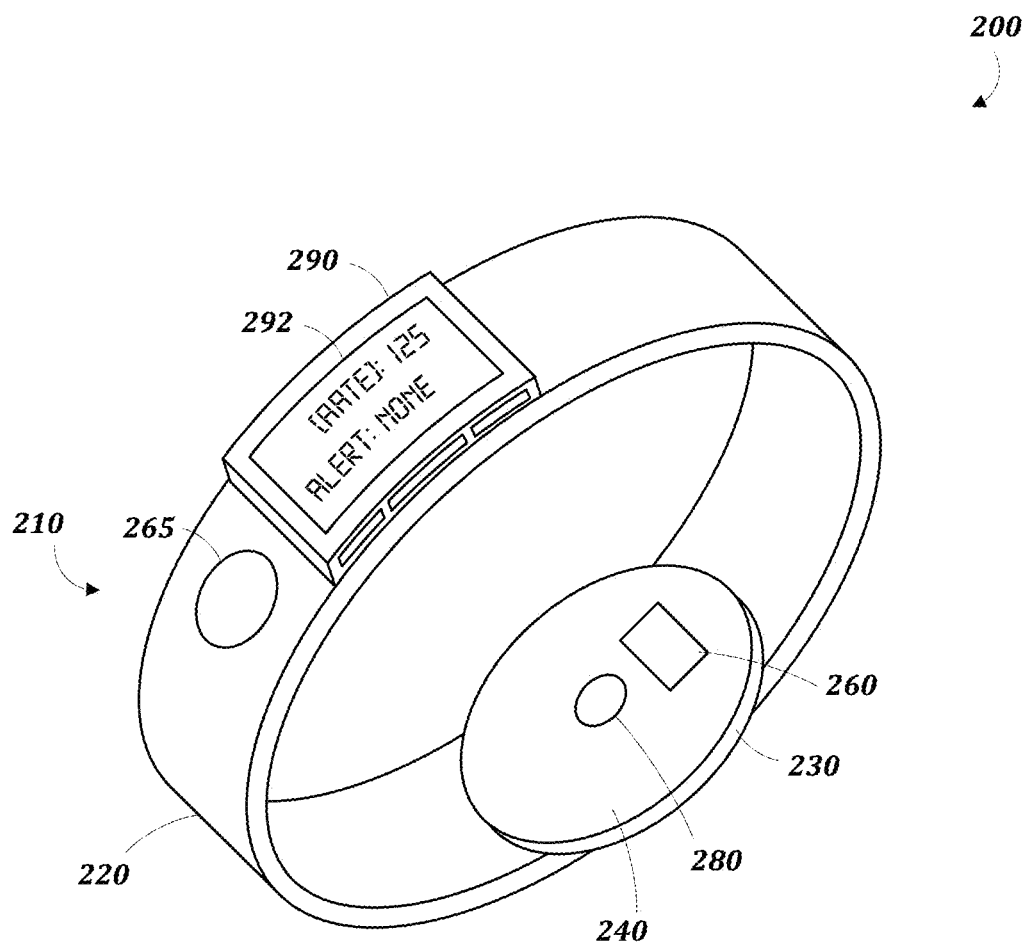
FIG. 2 illustrates a non-limiting example embodiment of a wearable device according to various aspects of the present disclosure.

One or more devices or systems could be configured to detect a signal, apply a cardiovascular classifier to the detected signal to determine whether a cardiovascular event is likely occurring, and, responsive to determining that a cardiovascular event is occurring, provide a prompt to a user (e.g., to touch an electrode on the device, to perform a clinical assessment or other activity) or perform some other activity (e.g., detect an electrocardiographic signal using two or more electrodes or electrical contacts of a wearable device). FIG. 2 illustrates a non-limiting example embodiment of a wearable device 200 according to various aspects of the present disclosure that can perform such operations, or other operations described herein.

The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where a signal related to a cardiovascular event may be detected (e.g., proximate a portion of subsurface vasculature or some other tissue containing pulsatile blood flow, proximate one or more skin locations from which an electrocardiographic signal may be extracted), the qualification of which will depend on the type of detection system used. The device may be placed in close proximity to skin or tissue, but need not be touching or in intimate contact therewith. A mount 210, such as a belt, wristband, ankle band, etc. can be provided to mount the device at, on or in proximity to the body surface. The mount 210 may prevent the wearable device from moving relative to the body to reduce measurement error and noise. In one example, shown in FIG. 2, the mount 210, may take the form of a strap or band 220 that can be worn around a part of the body. Further, the mount 210 may be an adhesive substrate for adhering the wearable device 200 to the body of a wearer.

A measurement platform 230 is disposed on the mount 210 such that it can be positioned on the body where subsurface vasculature is easily observable or where some other signal of interest may be detected. An inner face 240 of the measurement platform is intended to be mounted facing to the body surface. The measurement platform 230 may house first sensor 280, which may be configured to detect one or more signals related to occurrence of a cardiovascular event of interest (e.g., atrial or ventricular tachycardia, bradycardia, or fibrillation, acute hypotension, acute hypertension, or some other event related to the cardiovascular system of a person). For example, the first sensor 280 may include an optical sensor that is configured to detect a degree of absorption of light at one or more wavelengths by blood in a portion of subsurface vasculature over time (e.g., by illuminating the portion of subsurface vasculature and detecting an intensity or other properties of light responsively reflected by, scattered by, or otherwise emitted from the portion of subsurface vasculature). In another example, the first sensor 280 may include an accelerometer, a pressure sensor, or some other sensor configured to detect a blood pressure in the portion of subsurface vasculature, to detect a displacement of the skin surface related to changes in the volume or pressure of blood in the portion of subsurface vasculature or to motion of a body part (e.g., during exercise, walking, sleeping, or other activities), or to detect some other physical variable related to occurrence or non-occurrence of a cardiovascular event.

The measurement platform 230 may include multiple such sensors, and the signals detected using the sensor(s) could be substantially continuously related to a cardiovascular event or signal related thereto (e.g., related to a cardiovascular pulse or other physiological signal or process related to the cardiovascular pulse) or could be intermittently related to the cardiovascular event or signal related thereto (e.g., when the absolute or relative (to a target tissue, e.g., skin surface, portion of subsurface vasculature) motion of the sensor is minimal, when the sensor is in consistent contact with skin or with some other tissue). Further, the measurement platform 230 may include elements of sensors that are configured to operate to detect a signal that is related to the cardiovascular event when a wearer performs some action. For example, the measurement platform 230 includes a first electrode 260 that is configured to be in contact with skin of the wrist when the wearable device 200 is mounted to the wrist. The wearable device also includes a second electrode 265 that is disposed on the band 220 and that can be contacted by skin of an opposite arm (e.g., skin of a fingertip) of a wearer. When the device 200 is mounted to a wrist such that the first electrode 260 is in contact with skin of the wrist and the second electrode 265 is being contacted by skin of the opposite arm, an electrocardiographic signal could be detected by the device 200 using the electrodes 260, 265. The electrocardiographic signal could then be used to confirm whether the cardiovascular event is occurring, to detect some additional information about the cardiovascular event, or to facilitate some other application.

The wearable device 200 may also include a user interface 290 via which the wearer of the device may receive one or more recommendations, prompts, alerts, or other indications generated either from a remote server or other remote computing device, or from a processor within the device. For example, the user interface 290 could be used, in response to determining that a cardiovascular event is occurring or is likely to be occurring, to prompt the user to touch the second electrode 265 such that an electrocardiographic signal could be detected to provide additional information about such a cardiovascular event. The indications could be any indication that can be noticed by the person wearing the wearable device. For example, the indication could include a visual component (e.g., textual or graphical information on a display), an auditory component (e.g., an alarm sound), and/or tactile component (e.g., a vibration). Further, the user interface 290 may include a display 292 where a visual indication of the alert, prompt, or recommendation may be displayed. The display 292 may further be configured to provide an indication of the measured physiological parameters, for instance, a determined cardiovascular pulse rate.

A wearable device as described herein (e.g., wearable device 210) could be modular. That is, one or more components of such a wearable device could be replaceable, extensible, and/or otherwise reconfigurable to add and/or remove capabilities of the wearable device. For example, a wearable device could include a housing containing a battery, a communications interface, a touchscreen user interface, and general-purpose electronics to enable a variety of applications of a wearable device. The wearable device could further include a modular mount configured to mount the housing to an external body surface and to enable some applications of the wearable device, e.g., by including one or more sensors. For example, a first modular mount could be configured to mount the housing around a wrist of a wearer and to enable extraction of an electrocardiographic waveform from voltage fluctuations between the arms of a wearer by providing a second electrical contact on an outside surface of the mount (e.g., an outer surface of a frame encircling the housing) to complement a first electrical contact provided by the housing on an inside surface of the housing. A second modular mount could be configured to mount the housing around the chest of a wearer and to enable detection of breathing patterns of the wearer by providing a strain sensor in a band of the mount that encircles the chest of the wearer. Elements of such a modular device could be electrically connected via, e.g., spring-loaded contacts.

Figure 3:
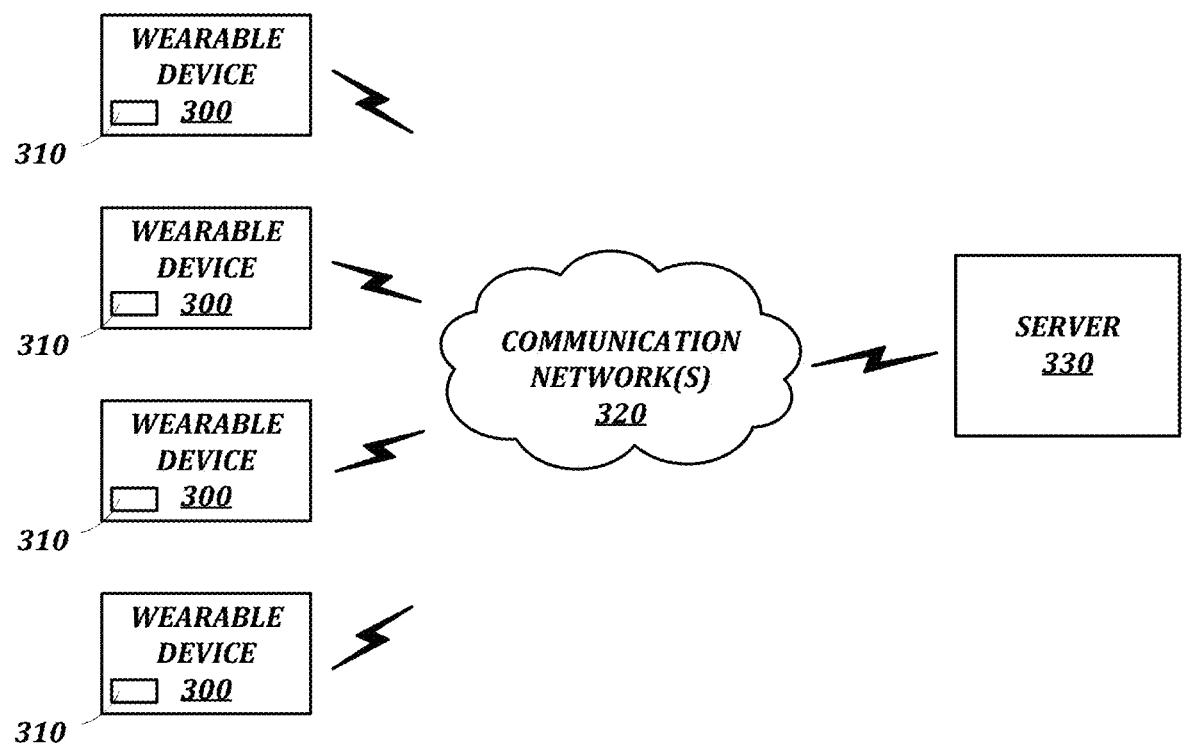
FIG. 3 is a simplified schematic drawing illustrating a non-limiting example embodiment of a system including one or more wearable devices according to various aspects of the present disclosure.

FIG. 3 is a simplified schematic drawing illustrating a non-limiting example embodiment of a system including one or more wearable devices 300 according to various aspects of the present disclosure. The one or more wearable devices 300 may be configured to transmit data via a communication interface 310 over one or more communication networks 320 to a remote server 330. In one embodiment, the communication interface 310 includes a wireless transceiver for sending and receiving communications to and from the server 330. In further embodiments, the communication interface 310 may include any means for the transfer of data, including both wired and wireless communications. For example, the communication interface may include a universal serial bus (USB) interface or a secure digital (SD) card interface. Communication networks 320 may be any one of may be one of: a plain old telephone service (POTS) network, a cellular network, a fiber network and a data network. The server 330 may include any type of remote computing device or remote cloud computing network. The server 330 may include a computing system that comprises one or more computing devices. Further, communication network 320 may include one or more intermediaries, including, for example wherein the wearable device 300 transmits data to a mobile phone or other personal computing device, which in turn transmits the data to the server 330.

In addition to receiving communications from the wearable device 300, such as collected physiological parameter data and data regarding health state as input by the user, the server may also be configured to gather and/or receive either from the wearable device 300 or from some other source, information regarding a wearer's overall medical history, environmental factors and geographical data. For example, a user account may be established on the server for every wearer that contains the wearer's medical history. Moreover, in some examples, the server 330 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GNSS system so that it can include GNSS location information (e.g., GPS coordinates) in a communication to the server. As another example, a wearable device may use a technique that involves triangulation (e.g., between base stations in a cellular network) to determine its location. Other location-determination techniques are also possible.

The server 330 may also be configured to make determinations regarding cardiovascular events of a user based on information received from one or more of the wearable devices 300 that are associated with the user. This could include receiving signals detected by multiple sensors of a single wearable device 300 and/or receiving signals from multiple devices 300 and using the received signals to determine some information about cardiovascular events of a user, e.g., about the existence, timing, or other properties of one or more such events, predictive properties or features of one or more sensor signals in relation to such events, or some other information. The server 330 could also determine information about the sensor signal(s) that could be used by one or more of the devices 300 to determine, based on such sensor signals, whether a cardiovascular event is occurring. For example, the server 330 could determine pattern-matching templates, filter cutoffs, parameters of a predictive algorithm, or some other information related to a cardiovascular classifier that could be transmitted to one of the devices 300. Such a cardiovascular classifier could then be used by the device 300 to predict, based on signals generated by one or more sensors of the device 300, to predict whether a cardiovascular event is occurring. The server 330 could generate such a cardiovascular classifier based on information received from the particular device 300 and/or based on information received from a population of devices 300. Further, the server 330 may periodically update such a cardiovascular classifier (e.g., based on additional sensor signals received from the device 300) and send the updated classifier to the device 300.

The server may also be configured to make determinations regarding drugs or other treatments received by a wearer of one or more of the devices 300 and, at least in part, the cardiovascular event data, detected electrocardiographic signals, and/or the indicated health state of the user. From this information, the server may be configured to derive an indication of the effectiveness of the drug or treatment. For example, if a wearer is prescribed a drug intended to treat tachycardia, but the server receives data from the wearable device(s) indicating (based on determined pulse rates) that the wearer's heart rate has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as cardiovascular classifiers or collected electrocardiographic signals, collected from his or her device may only be used for generating an individual baseline and recommendations in response to collection and comparison of his or her own data and may not be used in generating a population baseline or for use in population correlation studies.

Figure 4:
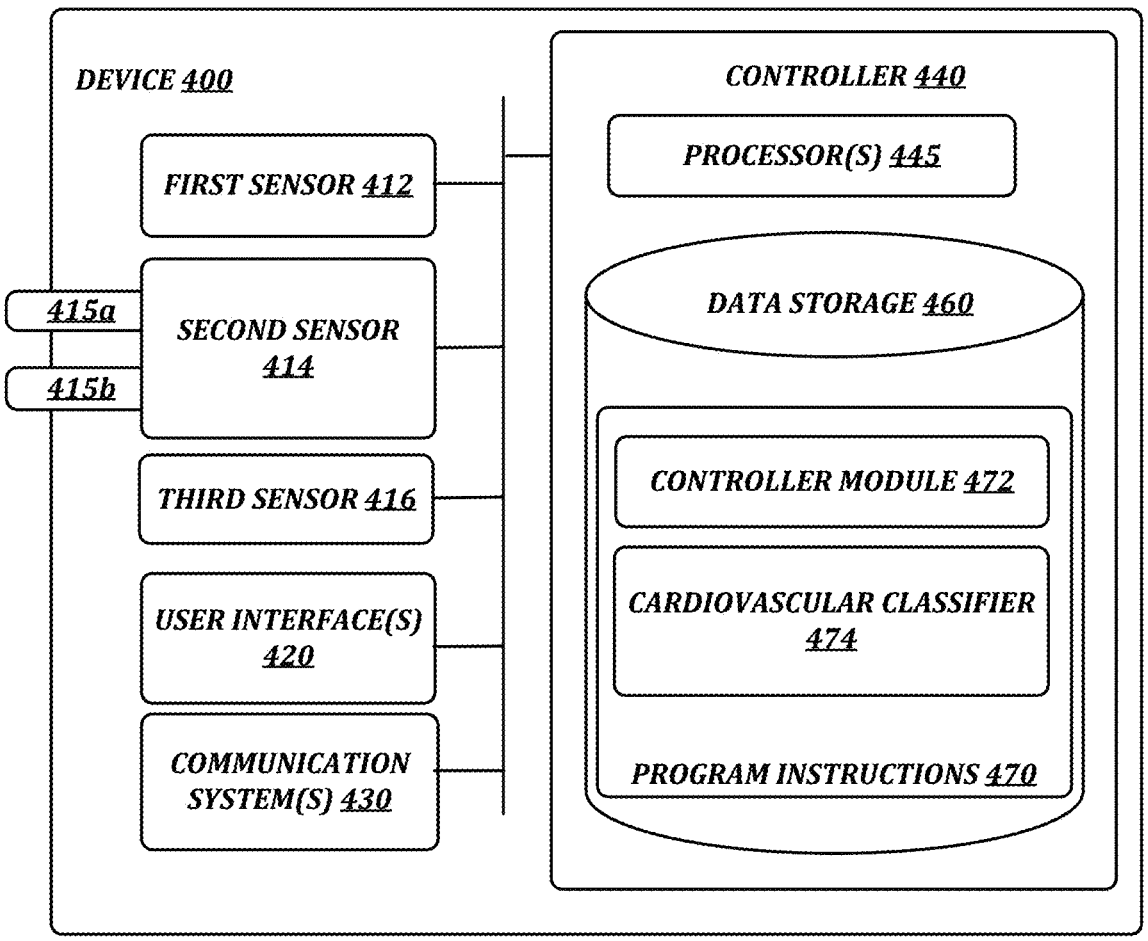
FIG. 4 is a simplified block diagram illustrating some components included in a non-limiting example embodiment of a device according to various aspects of the present disclosure.

FIG. 4 is a simplified block diagram illustrating some components included in a non-limiting example embodiment of a device 400 according to various aspects of the present disclosure. Device 400 may take the form of or be similar to the devices 110, 200 shown in FIGS. 1A, 1B, 1C and 2. That is, device 400 may take the form of a wrist-mountable or otherwise body-mountable device. Device 400 may also take other forms, e.g., could take the form of a device configured to be maintained in proximity to an environment of interest (e.g., a body part) by a user or operator of the device 400 or by a frame or other supporting structure. Device 400 could also take the form of a device configured to signals of interest from some other environment, for example, a body of an animal or some other environment containing a parameter or variable that contains an oscillating pattern having a frequency or rate that could be detected according to the methods described herein. Device 400 also could take other forms.

In particular, FIG. 4 shows an example of a device 400 having a first sensor 412, a second sensor 414, a third sensor 416, a user interface 420, communication system(s) 430 for transmitting data to a remote system, and a controller 440. The components of the device 400 may be disposed on a mount or on some other structure for mounting the device to enable stable detection of one or more signals related to a cardiovascular event (e.g., related to a cardiovascular pulse rate) or other process of interest, for example, around a wrist of a wearer such that signals related to a portion of subsurface vasculature or other target tissue are detectable.

Controller 440 may be provided, as illustrated, as a computing device that includes one or more processors 445 that are configured to execute computer-readable program instructions 470 that are stored in the computer readable data storage 460 and that are executable to provide the functionality of a device 400 described herein. In some embodiments, the controller 440 may be provided as an ASIC, FPGA, or other device that incorporates some or all of the logic embodied by the computer-readable program instructions 470 into circuitry.

The computer readable data storage 460 may include or take the form of one or more non-transitory, computer-readable storage media that can be read or accessed by at least one processor 445. The one or more computer-readable storage media can include volatile and/or non-volatile storage components, such as optical, magnetic, organic or other memory or disc storage, which can be integrated in whole or in part with at least one of the one or more processors 445. In some embodiments, the computer readable data storage 460 can be implemented using a single physical device (e.g., one optical, magnetic, organic or other memory or disc storage unit), while in other embodiments, the computer readable data storage 460 can be implemented using two or more physical devices.

The first 412, second 414, and third 416 sensors are configured to detect respective first, second, and third signals. As noted elsewhere herein, the first sensor 412 could detect a signal that is substantially continuously related to a cardiovascular pulse or other physiological properties or processes of a person such that the first signal can be used substantially continuously to estimate whether a specified cardiovascular event (e.g., an instance of atrial or ventricular tachycardia, fibrillation, bradycardia, or some other arrhythmia) is occurring. The second sensor 414 could detect a second signal that may be intermittently related to the cardiovascular event such that the second signal can be used to determine some information about the cardiovascular event (e.g., to verify that the event is occurring, to determine a electrocardiographic waveform of the heart during the event). For example, the second sensor 414 could include two (or more) electrical contacts or electrodes 415a, 415b that, when a wearer contacts the electrodes 415a, 415b of the second sensor 414 with skin of the wearer, could be used to detect an electrocardiographic signal related to the operation of the wearer's heart.

The first 412, second 414, and third 416 sensors could be provided on or within a single housing of the device 400 or within multiple housings (e.g., connected using a cable or other interconnection). The first 412, second 414, and third 416 sensors could include any of the types of sensors described elsewhere herein to detect signals that are at least intermittently related to a cardiovascular event or to some other property or process of interest.

The program instructions 470 stored on the computer readable data storage 460 may include instructions to perform any of the methods described herein. For instance, in the illustrated embodiment, program instructions 470 include a controller module 472 and a cardiovascular classifier 474.

The controller module 472 can include instructions for operating the first 412, second 414, and third 416 sensors. For example, the controller module 472 may include instructions for operating a light source and light sensor of the first sensor 412 at a plurality of points in time to obtain a respective plurality of samples of a photoplethysmographic signal. In another example, the third sensor could include at least one of an accelerometer or a gyroscope and the controller module 472 may include instructions for operating the third sensor 416 to measure signals related to a cardiovascular event or to some other signal or process of interest, e.g., to detect the motion and/or orientation of a body segment to which the third sensor 416 is mounted or otherwise mechanically coupled. The controller module 472 may include instructions for operating one or more of the sensors 412, 414, 416 to detect a signal that is not directly related to a cardiovascular event or other signal or interest but that may be related to the operation of the sensors 412, 414, 416 to detect such signals, e.g., to detect an impedance between electrodes that may be used, by the second sensor 414, to detect an electrocardiographic signal. In some examples, the controller module 472 may operate an analog-to-digital converter (ADC) to sample one or more signals (e.g., amplifier outputs) generated by the first 412, second 414, and/or third 416 sensors to obtain sets of samples of the signals detected during one or more periods of time.

The controller module 472 could further include instructions for determining that a signal detected by one of the sensors 412, 414, 416 is related to a signal of interest (e.g., an electrocardiographic signal) during a particular period of time. This could include detecting the presence or some other quality of features (e.g., QRS complexes of an electrocardiographic signal, peaks of a photoplethysmographic signal) in the signal, determining a degree of variability of pulse timing or pulse rates determined from the signal, determining a signal-to-noise ratio or other noise information about the signal, detecting a pressure applied to an external surface of the device 400, or using some other methods to generate features to be provided to the cardiovascular classifier 474. For example, the controller module 472 could include instructions to determine whether first and second electrical contacts of the second sensor 414 are in contact with skin and/or that an ECG waveform can be extracted from voltage fluctuations between such electrical contacts and to responsively extract an ECG waveform. This could include analyzing voltage fluctuations between the electrical contacts to determine whether the voltage fluctuations contain ECG waveforms. Additionally or alternatively, this could include actively or passively sensing an effective resistance and/or capacitance between the electrical contacts and further determining that the sensed resistance and/or capacitance corresponds to the electrical contacts being in contact with skin.

The controller module 472 can also include instructions for operating a user interface 420. For example, controller module 472 may include instructions for displaying data collected by the controller module 472, for presenting prompts to perform diagnostic tasks or other actions (e.g., contacting an electrode of the second sensor 414 to facilitate detection of an electrocardiographic signal), or for providing some other indications. Further, controller module 472 may include instructions to execute certain functions based on inputs accepted by the user interface 420, such as inputs accepted by one or more buttons or touchscreen displays disposed on the user interface.

The cardiovascular classifier 474 may include instructions for analyzing data (e.g., signals detected by the sensor(s) 412, 414, 416) to determine whether a cardiovascular event is occurring (e.g., to determine that a signal received from the sensor(s) is indicative of the cardiovascular event). In particular, the cardiovascular classifier 474 may include instructions for determining spectral contents, detecting features (e.g., heart beats), determining pulse rates or pulse timings, applying kernel methods (e.g., principal components analysis or independent components analysis kernels), for generating a priori or a posteriori probabilities, or for performing some other analyses related to determining, based on one or more sensor signals, whether a cardiovascular event is occurring. In particular, the cardiovascular classifier 474 may include algorithmic parameters, PCA or ICA kernels, polynomial coefficients, threshold values, templates for pattern matching, filter coefficients, or other information that could be used to determine whether a particular sensor signal or signals is indicative of a cardiovascular event. In some examples, the cardiovascular classifier 474 may include instructions for determining a particular activity of the user (e.g., exercising, sleeping, walking, sitting, eating) and determining whether a sensor signal is indicative of the cardiovascular event could include making such a determination based on the determined activity of the user (e.g., selecting a threshold value based on the determined activity, and applying the selected threshold value to a determined pulse rate to determine whether tachycardia or some other cardiovascular arrhythmic event is occurring).

Some of the program instructions of the controller module 472 and the cardiovascular classifier 474 may, in some examples, be stored in a computer-readable medium and executed by a processor located external to the device 400. For example, the device 400 could be configured to operate one or both of the sensors 412, 414, 416 (or to otherwise generate or obtain a plurality of samples of a signal related to a cardiovascular event) and then transmit related data to a remote server, which may include a mobile device, a personal computer, the cloud, or any other remote system, for further processing (e.g., for the detection of cardiovascular events and/or properties or signals related thereto using methods described herein).

User interface 420 could include indicators, displays, buttons, touchscreens, head-mounted displays, and/or other elements configured to present information about the device 400 to a user and/or to allow the user to operate the device 400. Additionally or alternatively, the device 400 could be configured to communicate with another system (e.g., a cellphone, a tablet, a computer, a remote server) and to present elements of a user interface using the remote system. The user interface 420 could be disposed proximate to the sensors 412, 414, 416 or other elements of the device 400 or could be disposed away from other elements of the device 400 and could further be in wired or wireless communication with the other elements of the device 400. The user interface 420 could be configured to allow a user to specify some operation, function, or property of operation of the device 400. The user interface 420 could be configured to present a determined pulse rate, cardiovascular event, or some other health state of a wearer of the device 400, or to present some other information to a user. For example, the user interface 420 could be operated, in response to determining that a cardiovascular event is occurring or is likely occurring, to prompt the wearer to perform some action related to the cardiovascular event (e.g., to perform a diagnostic task, to seek medical attention, to take a drug, to touch an electrical contact of the device 400). Other configurations and methods of operation of a user interface 420 are anticipated.

Communication system(s) 430 may also be operated by instructions within the program instructions 470, such as instructions for sending and/or receiving information via a wired or wireless medium using a transceiver, which may be disposed on or in the device 400. The communication system(s) 430 can optionally include one or more oscillators, mixers, frequency injectors, etc. to modulate and/or demodulate information on a carrier frequency to be transmitted and/or received by the antenna. In some examples, the device 400 is configured to indicate an output from the controller 440 by transmitting an electromagnetic or other wireless signal according to one or more wireless communications standards (e.g., Bluetooth, WiFi, IRdA, ZigBee, WiMAX, LTE) using communication system(s) 430. In some examples, the communication system(s) 430 could include one or more wired communications interfaces and the device 400 could be configured to indicate an output from the controller 440 by operating the one or more wired communications interfaces according to one or more wired communications standards (e.g., USB, FireWire, Ethernet, RS-232).

In some examples, obtained samples of a signal or other physiological property or parameter of interest, determined information about cardiovascular events, or other information generated by the device 400 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

Using Measurements of Inter-Beat Interval Entropy to Detect Atrial Fibrillation

Atrial fibrillation (AF) is a condition of the heart where the atria quiver and contract irregularly. Between 4 to 7 million people have AF in the United States; many are over 65 and hypertensive, or have other cardiovascular comorbidities. AF is the most common arrhythmia in adult populations. The prevalence is expected to continue to increase, reaching 12 million in the U.S. by year 2050. In addition to being widespread, AF contributes a significant cost burden to the healthcare system. Total AF-related direct spend in the U.S. is estimated to be $6.6 billion annually. However, AF detection is particularly sensitive to problems discussed above, in that existing metrics or features extracted from PPG data is not particularly reliable for detecting AF, and so it is difficult to obtain both adequate battery life and high-quality AF diagnostic information using a wearable device.

Currently in the marketplace, there is a lack of a noninvasive, long-term (i.e., >30 days) device for atrial fibrillation (AF) that incorporates clinically accepted signals (i.e., electrocardiogram). The absence of such a device has limited the ability of healthcare practitioners to know exactly if, when, and how much AF is occurring over the course of the patient's journey with his/her AF condition, thereby missing opportunities to deliver appropriate therapies in a timely manner or provide a feedback loop for existing rate/rhythm control strategies. "Silent", or asymptomatic, AF is also a problem leading to undiagnosed and untreated AF which is associated with a 5× increased risk of stroke. Current screening methods and tools (such as those described above) provide snapshot checks for AF, but are associated with a very low diagnostic yield due to the non-continuous data, which misses intermittent and unpredictable episodes of AF. Implantable devices such as pacemakers/ICDs and implantable loop recorders (ILRs) can technically provide this continuous data stream, but the high cost and invasive nature limit the market access and use case justification. A remote, low-cost, noninvasive technique to reliably monitor and detect AF on a long-term basis can fill the critical data gap needed to inform actionable medical interventions ultimately leading to improved patient outcomes.

In some embodiments of the present disclosure, features related to inter-beat intervals (IBI) detected by the PPG sensor of the wearable device 400 are extracted and provided to the cardiovascular classifier 474 in order to detect likely instances of AF. In addition to traditional features extracted from IBI data, some embodiments of the present disclosure also use features related to the entropy of the IBI data to improve the predictions generated by the cardiovascular classifier 474. In some embodiments, co-information between the IBI data and IBI data gathered from healthy and AF populations is determined in order to derive features that represent the probability that a given sample of IBI data represents AF or a normal sinus rhythm. Co-information is a value that indicates an amount of information shared by all random variables in one or more data sets. In response to determining likely instances of AF based on these features, the wearable device 400 may prompt the user to obtain clinically acceptable data, such as an ECG, to be transmitted to a remote server for review by a clinician.

In some embodiments, the entropy-related features allow exceedingly short time segments of IBI data (e.g., about 10 seconds) to be used to generate accurate predictions regarding the presence or absence of AF. Because PPG data does not provide reliable results if the subject is moving too much, the ability to obtain quality results from short time segments of IBI data when an otherwise active subject may be temporarily still helps the wearable device 400 to obtain meaningful data even for active subjects. Further, the simple nature of the calculations described below for representing and comparing the entropy information reduces the amount of processing power used to generate the features, thereby reducing battery consumption and improving battery life.

Figure 5A:
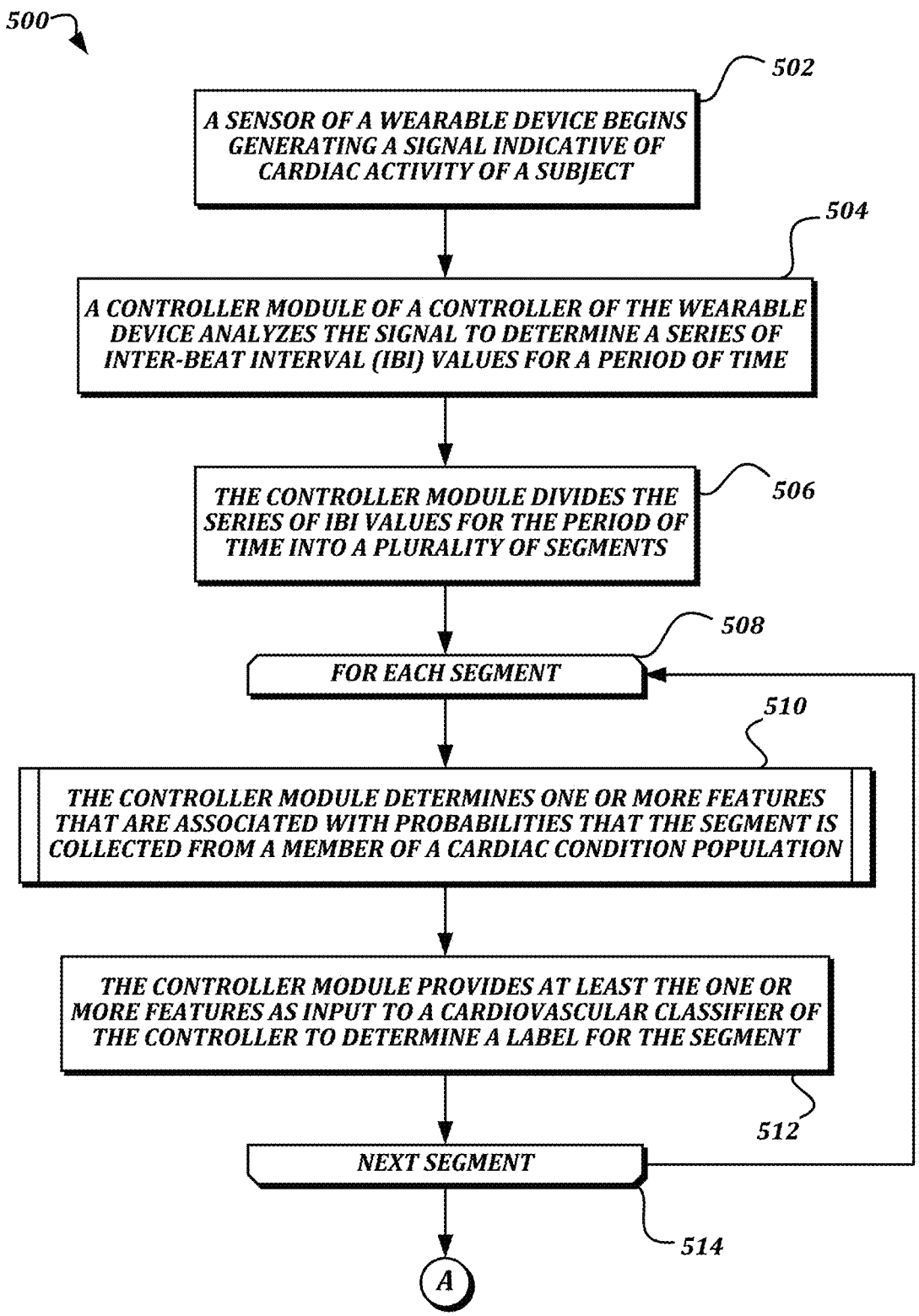
FIGS. 5A-5B are a flowchart that illustrates a non-limiting example embodiment of a method for monitoring cardiac activity of a subject in order to detect a cardiac condition according to various aspects of the present disclosure.
Figure 5B:
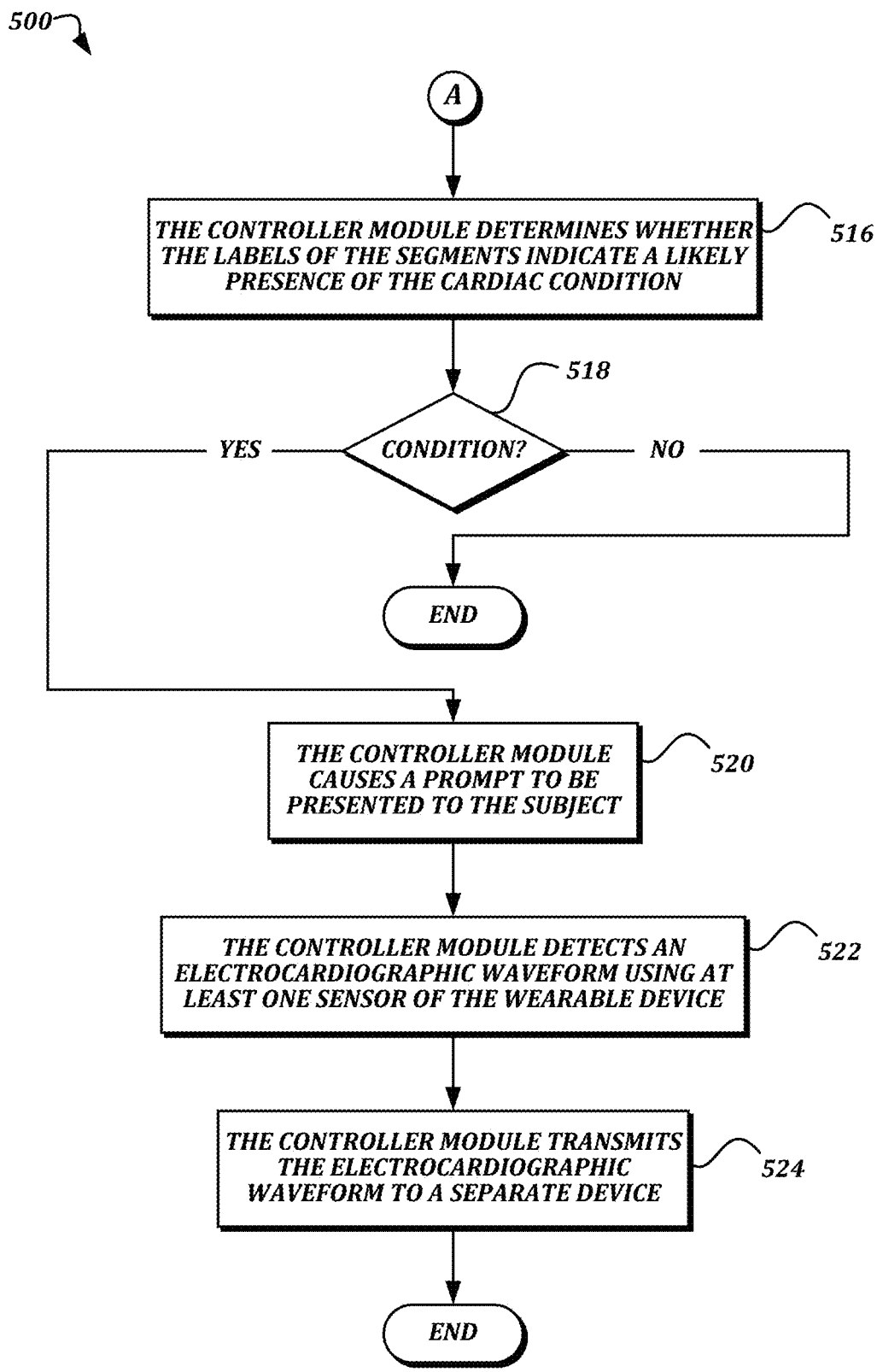

FIGS. 5A-5B are a flowchart that illustrates a non-limiting example embodiment of a method for monitoring cardiac activity of a subject in order to detect a cardiac condition according to various aspects of the present disclosure. Atrial fibrillation (AF) is one cardiac condition for which the method 500 is particularly suited, but should not be seen as limiting. Any other cardiac condition that can be detected based on features derived from a series of IBI values may be monitored using a similar method.

At block 502, a sensor 412 of a wearable device 400 begins generating a signal indicative of cardiac activity of a subject 100. In some embodiments, the sensor 412 is a PPG sensor, and the signal indicates heartbeats, provides a raw PPG value, or can otherwise be used to determine such information. In some embodiments, another type of sensor may be used from which similar data may be extracted.

At block 504, a controller module 472 of a controller 440 of the wearable device 400 analyzes the signal to determine a series of inter-beat interval (IBI) values for a period of time. In some embodiments, the signal may directly provide the series of IBI values, in which case the controller module 472 may simply store the series of IBI values received in the signal. In some embodiments, the controller module 472 may conduct signal processing to detect peaks in the signal in order to find the heartbeats, and may then measure an amount of time between the peaks in order to determine the IBI values. In some embodiments, the controller module 472 may use a different technique to extract the IBI values from the signal.

At block 506, the controller module 472 divides the series of IBI values for the period of time into a plurality of segments. In some embodiments, the controller module 472 may divide the series of IBI values into smaller segments of a predetermined time. For example, the period of time may be a long period of time, such as about 15 minutes, and the controller module 472 may divide the series of IBI values into a plurality of segments of a shorter period time, such as about 10 seconds. In some embodiments, the controller module 472 may divide the series of IBI values into smaller segments of a predetermined number of IBI values (e.g., 10 IBI values).

Conducting the processing over shorter segments provides various improvements to the overall result of the method 500. For example, a label applied to each segment may be considered a data point for determining whether the entire period of time includes the cardiac condition. If some of the segments include invalid data that must be discarded (e.g., if too much movement of the wearable device 400 is detected during the segment), using smaller segments allows a greater number of valid segments to remain to be the basis of the analysis. The further processing described below regarding the determination of features based on the segment can help provide accurate results for the shorter segments.

Figure 6:
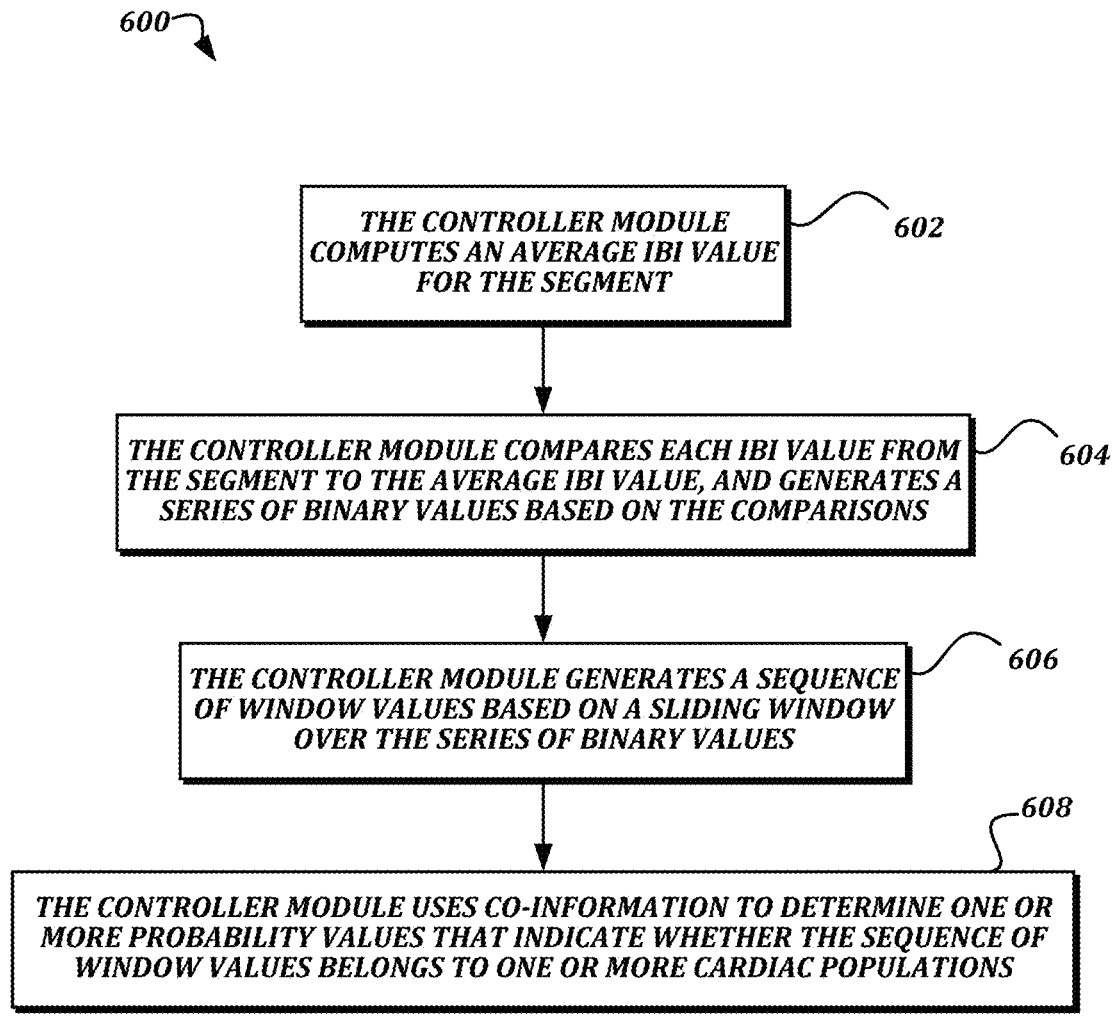
FIG. 6 is a flowchart that illustrates a non-limiting example embodiment of a procedure for determining features that represent probabilities that a series of IBI values was collected from a member of a cardiac condition population according to various aspects of the present disclosure.

The method 500 then proceeds to a for-loop defined between a for-loop start block 508 and a for-loop end block 514, wherein each segment of the plurality of segments is processed to determine a label for the segment. From the for-loop start block 508, the method 500 proceeds to procedure block 510, where the controller module 472 determines one or more features that are associated with probabilities that the segment is collected from a member of a cardiac condition population. Any suitable procedure may be used to determine the one or more features. One non-limiting example embodiment of a suitable procedure is illustrated in FIG. 6 and described further below. Typically, the procedure used at block 510 may use a comparison of the entropy of the segment to entropy typically observed in one or more populations to determine probabilities that the segments are similar to the one or more populations.

At block 512, the controller module 472 provides at least the one or more features as input to a cardiovascular classifier 474 of the controller 440 to determine a label for the segment. In some embodiments, the cardiovascular classifier 474 is trained to generate three different labels, depending on the input features. A first label indicates that the segment is likely to be associated with the cardiac condition being monitored (e.g., AF is present). A second label indicates that the segment is likely to not be associated with the cardiac condition being monitored (e.g., AF is not present, or a normal sinus rhythm (NSR) is present). A third label indicates that the segment is not confidently determined to be in either group.

In some embodiments, the one or more features determined in procedure block 510 may be provided as input to the cardiovascular classifier 474 along with other features. For example, other features can be extracted from the series of IBI values in the segment, and provided as additional input features. Some non-limiting examples of features that may be extracted from the series of IBI values in the segment include a normalized IBI value or mean IBI value, a standard deviation of the IBI values, a standard deviation of a differential of the IBI values, a kurtosis of a differential of the IBI values, and an SD1 and/or SD2 value of a Poincare plot of the IBI values. In some embodiments, features obtained from other data may be provided to the cardiovascular classifier 474 as well. For example, features may be extracted from signals produced by an accelerometer of the device 400 in order to allow the cardiovascular classifier 474 to discard or discount segments that are associated with too much movement of the device 400 (which reduces the accuracy of the PPG data).

The method 500 then proceeds to the for-loop end block 514. If further segments remain to be processed, then the method 500 returns to the for-loop start block 508 to process the next segment. Otherwise, if all of the segments have been processed, then the method 500 proceeds from the for-loop end block 514 to a continuation terminal ("terminal A").

From terminal A (FIG. 5B), the method 500 proceeds to block 516, where the controller module 472 determines whether the labels of the segments indicate a likely presence of the cardiac condition. In some embodiments, the controller module 472 may base the determination on a threshold number (e.g., more than half) of total labeled segments being labeled as likely indicating presence of the cardiac condition. In some embodiments, the controller module 472 may base the determination on whether a predetermined number of consecutive segments are labeled as likely indicating presence of the cardiac condition. In some embodiments, the threshold number or predetermined number may be determined by analyzing data collected from known populations.

At decision block 518, a determination is made based on whether the labels of the segments were determined to indicate a likely presence of the cardiac condition. If it was not determined that the cardiac condition is likely present, then the result of decision block 518 is NO, and the method 500 proceeds to an end block and terminates. In some embodiments, instead of terminating, the method 500 may return to the start and continue monitoring for the cardiac condition in a new time period. Otherwise, if it was determined that the cardiac condition is likely present, then the result of decision block 518 is YES, and the method 500 proceeds to block 520.

At block 520, the controller module 472 causes a prompt to be presented to the subject 100. In some embodiments, the prompt may direct the subject 100 to place a finger of a hand of an arm which is not wearing the device 400 on the second sensor 414 of the device 400 in order to enable the second sensor 414 to collect an electrocardiographic waveform. At block 522, the controller module 472 detects an electrocardiographic waveform using at least one sensor 414 of the wearable device 400. At block 524, the controller module 472 transmits the electrocardiographic waveform to a separate device. In some embodiments, the separate device may be a remote server 330. In some embodiments, the separate device may be a local computing device such as a desktop computing device, a tablet computing device, or a mobile computing device. In some embodiments, the controller module 472 may transmit the electrocardiographic waveform via an intermediate device, such as a smartphone. The electrocardiographic waveform may then be inspected by a clinician, by a signal processing device, or by any other suitable technique to look for signs of AF in the detailed waveform. Because the entropy-related features described above increase the accuracy of the processing of the PPG signals, the subject 100 should only be prompted to collect the ECG waveform when there is a significantly high likelihood that the ECG waveform will show the presence of AF.

The method 500 then proceeds to an end block and terminates.

The method 500 in FIGS. 5A-5B is illustrated as collecting a series of IBI values for a time period, and then splitting the series of IBI values into smaller segments. Because the segments are processed independently, in some embodiments, each segment may be processed contemporaneously with its collection, and the labels for each segment may be the only additional information to be stored by the device 400. The method 500 may then execute the actions of block 516 (and later) once a predetermined number of segments have been processed. In such embodiments, the actions of block 516 (and later) may be automatically executed at predetermined time intervals.

FIG. 6 is a flowchart that illustrates a non-limiting example embodiment of a procedure for determining features that represent probabilities that a series of IBI values was collected from a member of a cardiac condition population according to various aspects of the present disclosure. The procedure 600 is an example of a procedure suitable for use at procedure block 510 in FIG. 5A. The procedure 600 determines a measure of entropy for the series of IBI values (which are typically a segment of a longer series of IBI values, but can be any series of IBI values), and then uses co-information to determine how similar the entropy of the series of IBI values is to the entropy of similar data collected from one or more known populations. The procedure 600 uses this similarity to provide the probabilities that the series of IBI values are taken from each of the one or more known populations. FIGS. 7A-7C illustrate a non-limiting example embodiment of the results of the procedure 600 being executed over a given series of IBI values, and will be referred to throughout the discussion of the procedure 600.

At block 602, the controller module 472 computes an average IBI value for the segment. The average IBI value may be the arithmetic mean, the median, or any other suitable average value. FIG. 7A illustrates a not-to-scale heartbeat waveform with example IBI values listed below the waveform. The arithmetic mean of the IBI values for the series of IVI values is listed below the IBI values. Though FIG. 7A shows a waveform that appears to be a normal sinus rhythm ECG waveform, this is provided merely to illustrate that heartrate information is being processed. In some embodiments, any suitable waveform or data that can be processed to determine a series of IBI values may be used. Further, though the segment illustrated in FIG. 7A shows seven IBI values, this is a non-limiting example of a length of a segment, and in some embodiments, the segment may include more or fewer than seven IBI values.

Returning to FIG. 6, at block 604, the controller module 472 compares each IBI value from the segment to the average IBI value, and generates a series of binary values based on the comparisons. In some embodiments, the comparison may determine whether or not the IBI value is greater than the average IBI value. If the IBI value is greater than the average IBI value, then a binary 1 value may be generated. If the IBI value is not greater than the average IBI value, then a binary 0 value may be generated. In some embodiments, the comparison may be whether or not the MI value is greater than or equal to the average IBI value, and/or the binary values may be reversed, without departing from the scope of the present disclosure. In some embodiments, a different comparison may be made in order to generate the series of binary values that reflect the entropy of the segment. For example, in some embodiments, instead of comparing each IBI value to the average IBI value, each IBI value may instead be compared to the previous IBI value. While a different series of IBI values would be generated using this technique, certain characteristics in the resulting series would be retained. For example, if the IBI values in the segment were consistently rising or falling then there would be repetitions of "0" values or "1" values in the series, whereas if the IBI values were of inconsistently varying lengths, there would be fewer repetitions of "0" values or "1" values.

FIG. 7B illustrates the generation of a series of binary values for the series of IBI values indicated in FIG. 7A. As shown, the first, second, and third IBI values in the series of IBI values are less than the average IBI value, and so binary 0 values are placed in the sequence for those IBI values. The fourth and fifth IBI values in the series of IBI values are greater than the average IBI value, and so binary 1 values are placed in the sequence for those IBI values. The sixth IBI value in the series of IBI values is less than the average IBI value, and so a binary 0 value is placed in the sixth position in the sequence. The seventh IBI value in the series of IBI values is greater than the average IBI value, and so a binary 1 value is placed in the seventh position in the sequence.

Returning to FIG. 6, at block 606, the controller module 472 generates a sequence of window values based on a sliding window over the series of binary values. In some embodiments, the sliding window takes a predetermined number of binary values at a time from the series of binary values, and combines the binary values to a single binary number before moving the sliding window. In FIG. 7B, a sliding window of five values is used, thereby generating a series of 5-bit binary numbers. As illustrated, Window One includes the first five binary values ("00011"), and so the first window value is "00011" in binary, or "3" in base 10. The sliding window then moves over one value, such that Window Two includes binary values 2-6 ("00110"). Accordingly, the second window value is "00110" in binary, or "6" in base 10. The sliding window then moves over one more value, such that Window Three includes binary values 3-7 ("01101"). Accordingly, the third window value is "01101" in binary, or "13" in base 10. The calculated window values are illustrated in the table in FIG. 7C. The use of five values is a non-limiting example only, and in some embodiments, more or fewer values are used for the length of the sliding window. Further, the shifting of the sliding window by a single value is an example only, and in some embodiments, the sliding window may be shifted by more than a single value. Once the end of the sliding window reaches the last value in the series of binary values, the sequence of window values may end.

At block 608, the controller module 472 uses co-information to determine one or more probability values that indicate whether the sequence of window values belongs to one or more cardiac populations. In some embodiments, a data store includes records of sequences of window values recorded for one or more populations. For example, the data store may include records of sequences of window values that were determined from data collected form a first population that is known to experience a cardiac condition such as atrial fibrillation. The data store may also include records of sequences of window values that were determined from data collected from a second population that is known to not experience a cardiac condition such as atrial fibrillation (in other words, from a healthy population, or a population that experiences a normal sinus rhythm). The co-information can determine how similar the entropy (as represented by the sequence of window values calculated in block 606) is to the entropy of each population (as represented by the stored sequences of window values, and thereby generate probabilities regarding whether the series of IBI values includes an incidence of the cardiac condition or not.

Figure 8A:
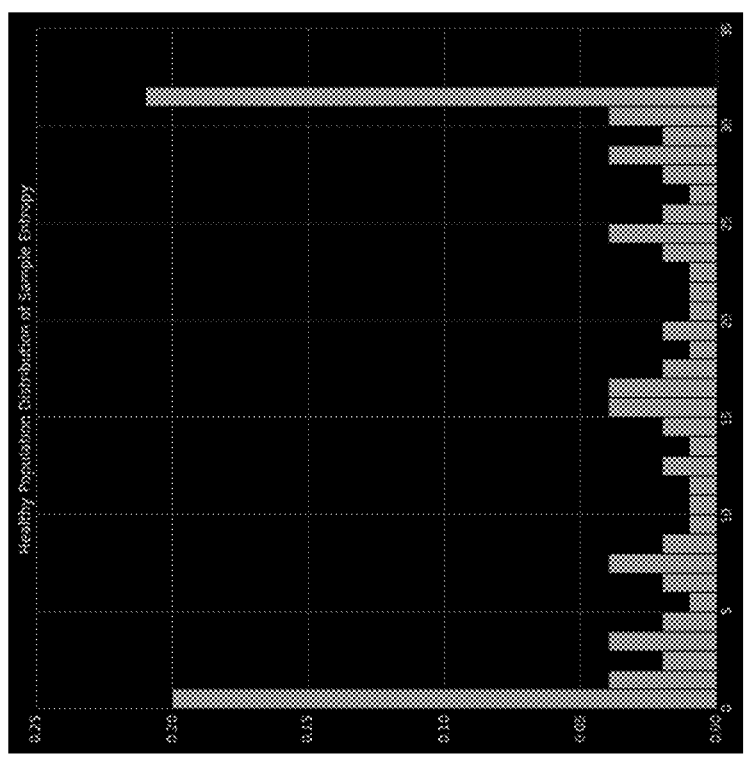
FIG. 8A illustrates a non-limiting example distribution of window values for a healthy population exhibiting normal sinus rhythm.
Figure 8B:
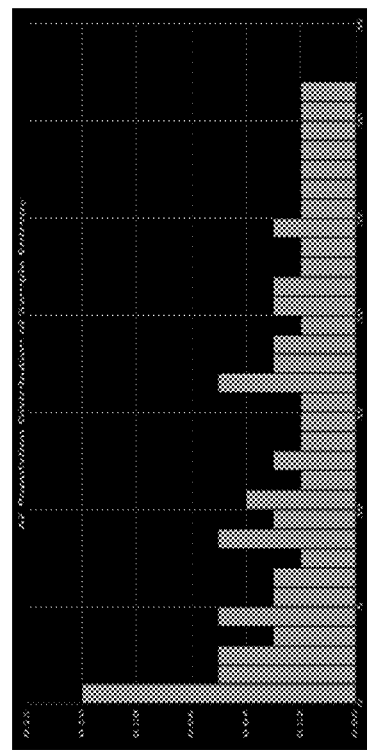
FIG. 8B illustrates a non-limiting example distribution of window values for a population exhibiting atrial fibrillation.

One basic intuition behind this determination is that for a normal sinus rhythm, the heartrate will generally be trending up or trending down, while during atrial fibrillation, the IBI values change more erratically. Accordingly, the entropy of the IBI values in the normal sinus rhythm will have a first pattern, and the entropy of the IBI values in atrial fibrillation will have a second pattern. These patterns can be easily captured with low computational cost using the sliding windows, since the normal sinus rhythm will likely exhibit long runs of being either below or above the average value, while the atrial fibrillation data will likely lack such long runs. For a five-bit window length, this will cause the distribution of the window values of the normal sinus rhythm to have peaks around 0 (a long run of zeros) and 31 (a long run of ones), while the atrial fibrillation data will lack such peaks. FIG. 8A illustrates a non-limiting example distribution of window values for a healthy population exhibiting normal sinus rhythm, and FIG. 8B illustrates a non-limiting example distribution of window values for a population exhibiting atrial fibrillation. As can be seen, the healthy population has peaks where the values 0 and 31 appear around 20% of the time each (with no other value appearing more than 4% of the time and many values appearing only 1% of the time), while the highest peak in the atrial fibrillation population is only 10%, and no value appears less than 2% of the time.

Beyond the distributions of window values, the sequences of the window values encode further information. For example, the normal sinus rhythm will be likely to have a run of zeros, followed by a one, a three, a seven, and a fifteen before a run of thirty-ones (reflecting the crossover between a run of zeros and a run of ones), or the reverse, while the atrial fibrillation data will be unlikely to have such a pattern. Determination of the co-information can extract these patterns and calculate the probabilities based thereon.

Returning to FIG. 6, the procedure 600 returns the one or more probability values, and terminates.

The discussion above describes determining features by using entropy to determine probabilities that sequences of IBI values belong to one or more populations associated with a cardiac condition, and then using those features as input to a cardiovascular classifier 474 to label a sequence of IBI values as exhibiting the cardiac condition, not exhibiting the cardiac condition, or being unknown. One will recognize that similar features can be calculated for labeled training data, and the features calculated for the training data can be used to train the cardiovascular classifier 474. For example, in some embodiments, multiple series of IBI values may be obtained from a known population of healthy individuals. Sequences of window values may be calculated for the multiple series and stored in a data store. Likewise, multiple series of IBI values may be obtained from a known population of individuals experiencing atrial fibrillation, and may be processed similarly. Thereafter, features can be extracted from each labeled series of IBI values (including the entropy-related features and the other features discussed in block 512), and these features can be used to train the cardiovascular classifier 474 using techniques described above.

In some embodiments as described above, the training of the cardiovascular classifier 474 may occur on the remote server 330. The cardiovascular classifier 474 may then be transmitted to the wearable device 400 from the remote server 330. The remote server 330 may, over time, receive additional data from the wearable devices 300, and may retrain the cardiovascular classifier 474 based on the additional data. The retrained cardiovascular classifier 474 may then be redistributed to the wearable devices 300.

While illustrative embodiments have been illustrated and described, it will be appreciated that various changes can be made therein without departing from the spirit and scope of the invention.

The embodiments of the invention in which an exclusive property or privilege is claimed are defined as follows:

1. A wearable device, comprising:
   a first sensor;
   a second sensor; and
   a controller having logic configured to, in response to execution by the controller, cause the wearable device to perform actions comprising:
      analyzing a signal generated by the first sensor to determine a series of heartbeat characteristic values for a subject;
      comparing the series of heartbeat characteristic values to a threshold value to generate a series of binary values that indicate whether or not each heartbeat characteristic value is greater than the threshold value;

generating a sequence of window values for the subject by moving a sliding window along the series of binary values to combine groups of binary values from the series of binary values into single numbers to be used as the window values;

comparing entropy in the sequence of window values for the subject to entropy in sequences of window values for a population associated with a cardiac condition to determine one or more features representing probabilities that the series of heartbeat characteristic values for the subject is similar to the series of heartbeat characteristic values for the population;

providing the features to a cardiovascular classifier to determine whether the series of heartbeat characteristic values for the subject is associated with the cardiac condition; and in response to determining that the series of heartbeat characteristic values for the subject is associated with the cardiac condition, collecting information using the second sensor.

2. The wearable device of claim 1, wherein the first sensor is a photoplethysmographic sensor, and wherein the second sensor is an electrocardiographic sensor.

3. The wearable device of claim 1, wherein the actions further comprise transmitting the information collected using the second sensor to a separate device.

4. The wearable device of claim 1, wherein the series of heartbeat characteristic values is a series of inter-beat interval (IBI) values, and wherein the threshold value is an average IBI value for at least a portion of the series of IBI values.

5. The wearable device of claim 1, wherein comparing entropy in the sequence of window values for the subject to entropy in the sequences of window values for the population associated with the cardiac condition includes comparing a co-information of the sequence of window values for the subject and at least one co-information of the sequences of window values for the population associated with the cardiac condition, wherein each co-information is a value that indicates an amount of information shared by all random variables in the corresponding sequences of window values.

6. The wearable device of claim 1, wherein the population is a first population, wherein the first population is known to experience the cardiac condition, wherein the one or more features represent first probabilities, and wherein the actions further comprise:

comparing entropy in the sequence of window values for the subject to entropy in sequences of window values for a second population to determine one or more second features representing probabilities that the series of heartbeat characteristic values for the subject is similar to the series of heartbeat characteristic values for the second population; and providing the one or more second features as additional features to the cardiovascular classifier;

wherein the second population is known to not experience the cardiac condition.

7. A non-transitory computer-readable medium having computer-executable instructions stored thereon that, in response to execution by one or more processors of a computing device, cause the computing device to perform actions for detecting a cardiac condition, the actions comprising:

computing, by the computing device, an average inter-beat interval (IBI) value for a series of IBI values from a first time segment;

creating, by the computing device, a series of binary values that indicate whether or not each IBI value of the series of IBI values is greater than the average IBI value;

generating, by the computing device, a sequence of window values by moving a sliding window along the series of binary values to combine groups of binary values from the series of binary values into single numbers to be used as window values;

determining, by the computing device, one or more features representing probabilities of whether the sequence of window values belongs to a data set associated with the cardiac condition; and providing, by the computing device, the features to a cardiovascular classifier to determine a label that indicates whether the first time segment is associated with the cardiac condition.

8. The computer-readable medium of claim 7, wherein determining the one or more features representing probabilities of whether the sequence of window values belongs to a data set associated with the cardiac condition includes:

comparing the sequence of window values to a data set that includes sequences of window values collected from a population of subjects that are known to exhibit the cardiac condition.

9. The computer-readable medium of claim 8, wherein comparing the sequence of window values to the data set that includes sequences of window values collected from the population of subjects that are known to exhibit the cardiac condition includes comparing a co-information of the sequence of window values and at least one co-information of the sequences of window values of the data set, wherein each co-information is a value that indicates an amount of information shared by all random variables in the corresponding sequences of window values.

10. The computer-readable medium of claim 8, wherein determining the one or more features representing probabilities of whether the sequence of window values belongs to a data set associated with the cardiac condition includes determining one or more features representing first probabilities of whether the sequence of window values belongs to a first data set associated with subjects that are known to exhibit the cardiac condition; and wherein the actions further comprise:

determining one or more features representing second probabilities of whether the sequence of window values belongs to a second data set associated with subjects that are known to not exhibit the cardiac condition; and providing the one or more features representing the second probabilities to the cardiovascular classifier.

11. The computer-readable medium of claim 7, wherein the first time segment is included in a plurality of time segments over a time period, and wherein the actions further comprise:

determining labels for each of the time segments in the plurality of time segments that indicate whether the time segments each are associated with the cardiac condition; and determining, based on the labels of the plurality of time segments, whether the time period is likely to represent a subject experiencing the cardiac condition.

12. The computer-readable medium of claim 11, wherein the actions further comprise, in response to determining that the time period is likely to represent a subject experiencing the cardiac condition, collecting electrocardiogram (ECG) data.

13. The computer-readable medium of claim 11, wherein the label for each time segment of the plurality of time segments is determined after the time segment has ended and while data for subsequent time segments is being collected.

14. The computer-readable medium of claim 11, wherein data for an entirety of the time period is collected before being separated into time segments and labeled.

15. A non-transitory computer-readable medium having computer-executable instructions stored thereon that, in response to execution by one or more processors of a computing system, cause the computing system to perform actions for training a cardiovascular classifier to detect a cardiac condition, the actions comprising:

receiving, by a computing system, a series of inter-beat interval (IBI) values collected from subjects of at least one population associated with the cardiac condition;

generating, by the computing system, representations of entropy within the series of IBI values, wherein generating representations of entropy within the series of IBI values includes, for at least a portion of the series of IBI values:

comparing each IBI value to a threshold value to create a series of binary values that indicate whether or not each IBI value is greater than the threshold value; and generating a sequence of window values by moving a sliding window along the series of binary values to combine groups of binary values from the series of binary values into single numbers to be used as the window values;

storing, by the computing system, the representations of entropy in a data store associated with the at least one population;

for each subject:

comparing, by the computing system, a representation of entropy in at least a portion of the series of IBI values for the subject with the representations of entropy in the data store associated with the at least one population to determine a feature that represents a probability that the portion of the series of IBI values is associated with the representations of entropy in the data store;

storing, by the computing system, the feature associated with the subject in a set of training data; and training, by the computing system, a cardiovascular classifier using the set of training data.

16. The computer-readable medium of claim 15, wherein the at least one population includes a first population of subjects who are known to experience the cardiac condition and a second population of subjects who are known to not experience the cardiac condition.

17. The computer-readable medium of claim 16, wherein comparing the representation of entropy in at least the portion of the series of IBI values for the subject with the representations of entropy in the data store associated with the at least one population to determine the probability that the portion of the series of IBI values is associated with the representations of entropy in the data store includes:

comparing the representation of entropy in at least the portion of the series of IBI values for the subject with the representations of entropy in the data store associated with the first population to determine a feature representing a first probability that the portion of the series of IBI values is associated with the representations of entropy of the first population; and comparing the representation of entropy in at least the portion of the series of IBI values for the subject with the representations of entropy in the data store associated with the second population to determine a feature representing a second probability that the portion of the series of IBI values is associated with the representations of entropy of the second population.

18. The computer-readable medium of claim 17, wherein storing the feature associated with the subject in the set of training data includes storing the feature representing the first probability and the feature representing the second probability associated with the subject in the set of training data.

19. The computer-readable medium of claim 15, wherein generating representations of entropy within the series of IBI values includes, for at least a portion of the series of IBI values:

computing an average IBI value;

wherein the threshold value is the average IBI value.

20. The computer-readable medium of claim 15, wherein comparing the representation of entropy in at least the portion of the series of IBI values for the subject with the representations of entropy in the data store associated with the at least one population to determine the feature representing the probability that the portion of the series of IBI values is associated with the representations of entropy in the data store includes:

comparing a co-information of the sequence of window values with at least one co-information in the data store, wherein each co-information is a value that indicates an amount of information shared by all random variables in the corresponding sequence of window values.

* * * * *